United States Patent [19]

Morioka et al.

[11] 4,447,309
[45] May 8, 1984

[54] PH SENSOR

[75] Inventors: Akihiro Morioka; Yuji Maeda; Tetsuro Matsumoto; Masakazu Yukinari; Eiichi Kishida, all of Tokyo, Japan

[73] Assignee: Yokogawa Hokushin Electric Corporation, Tokyo, Japan

[21] Appl. No.: 406,513

[22] Filed: Aug. 9, 1982

[30] Foreign Application Priority Data

Oct. 7, 1981 [JP] Japan .............................. 56-159707

[51] Int. Cl.³ ....................... G01N 27/30; G01N 27/38
[52] U.S. Cl. .................................... 204/402; 204/420; 204/433; 204/435; 324/438
[58] Field of Search ............... 204/402, 433, 420, 1 H, 204/435; 324/438

[56] References Cited

U.S. PATENT DOCUMENTS

| 2,415,067 | 1/1947 | Wallace ...................... 204/402 |
| 3,103,480 | 9/1963 | Watanabe et al. ............ 204/433 X |
| 3,216,915 | 11/1965 | Arthur et al. .............. 204/402 |
| 4,008,141 | 2/1977 | Kotani et al. ............... 204/433 X |
| 4,285,792 | 8/1981 | McGandy .................... 204/402 |

FOREIGN PATENT DOCUMENTS 7400640 10/1974 Netherlands ...................... 324/438

OTHER PUBLICATIONS

Dante Del Corso et al., IEEE Trans. on Instrum. and Measurement, vol. IM-26, No. 2, pp. 143-147, (1977).

Primary Examiner—G. L. Kaplan
Attorney, Agent, or Firm—Moonray Kojima

[57] ABSTRACT

A pH sensor comprising a sleeve assembly having at least first and second spaces, a partition separating the two spaces from each other with a water tight seal, and a barrel including a flange, a reference electrode accommodated in the first space and including a liquid junction, a glass electrode having a sensor unit disposed adjacent to the liquid junction, liquid grounding means mounted adjacent to the liquid junction, and a cable disposed in the second space with a watertight seal, the cable being electrically connected to the reference electrode, glass electrode and liquid grounding means. The pH sensor can be used for continuous flow, immersion or submersion types of installations, and can be fabricated inexpensively and is easily maintained. The sensor unit of the pH sensor can be easily cleaned by a cleaning unit which includes a rotatable shaft to which is connected a vane and a brush at one end. Fluid is impinged on the vane to cause rotation of the shaft and brush, lifts the brush against the sensor unit, and is ejected out of the shaft to clean the sensor unit and brush. A simple attachment can be used to connect the cleaning unit to the pH sensor to enable rapid, easily and reliable cleaning, and to enable rapid replacement of such cleaning unit.

11 Claims, 21 Drawing Figures

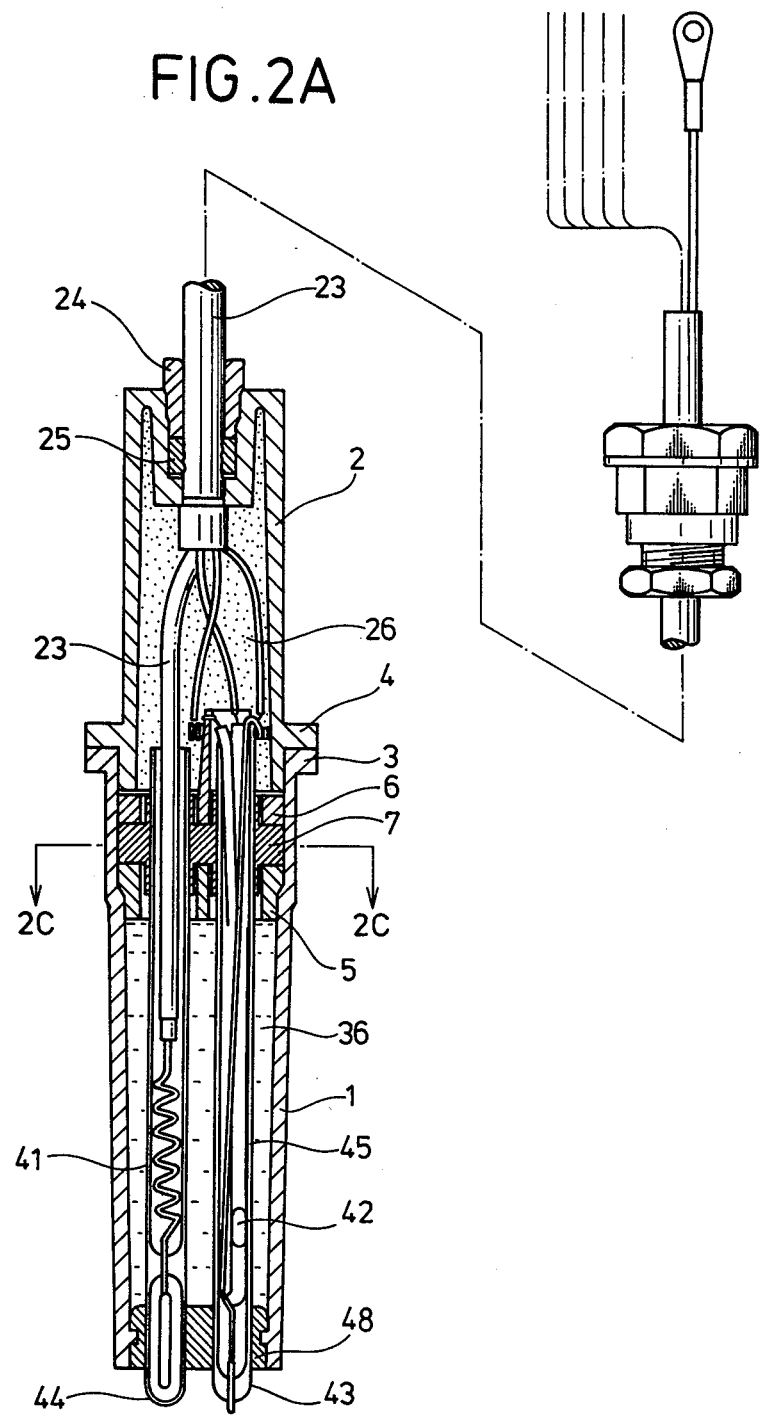

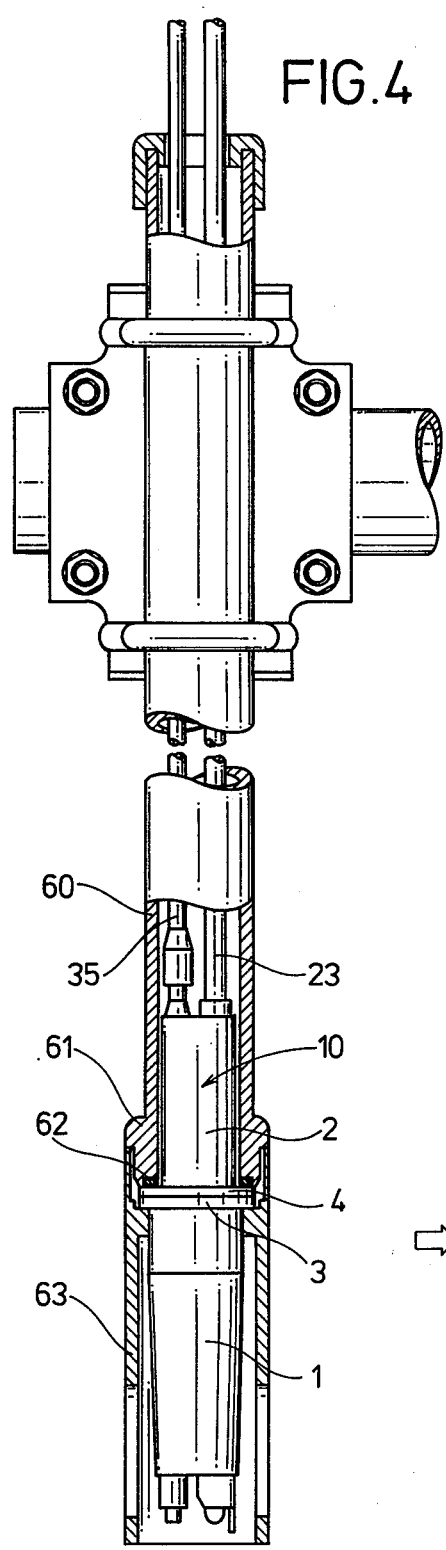
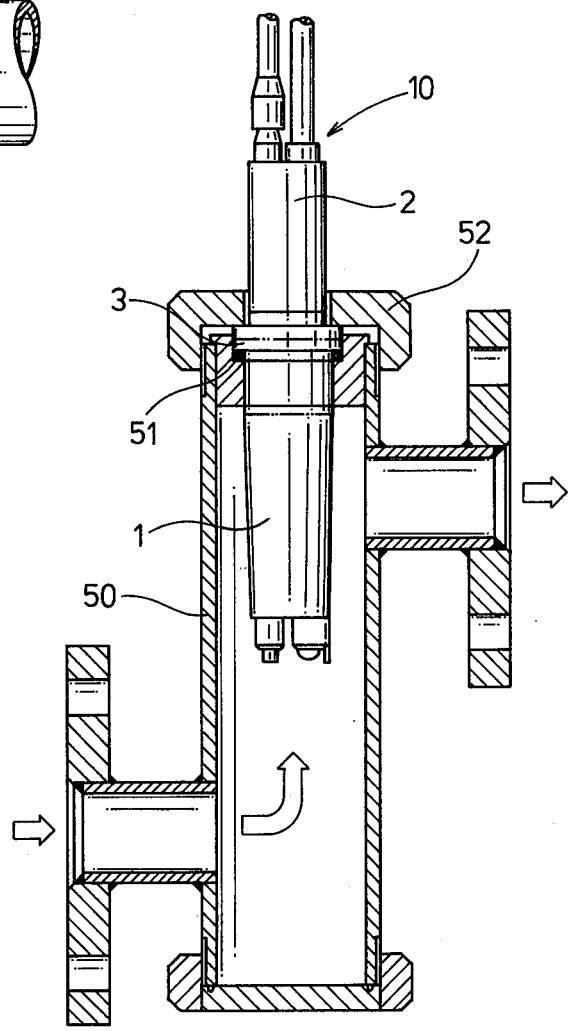

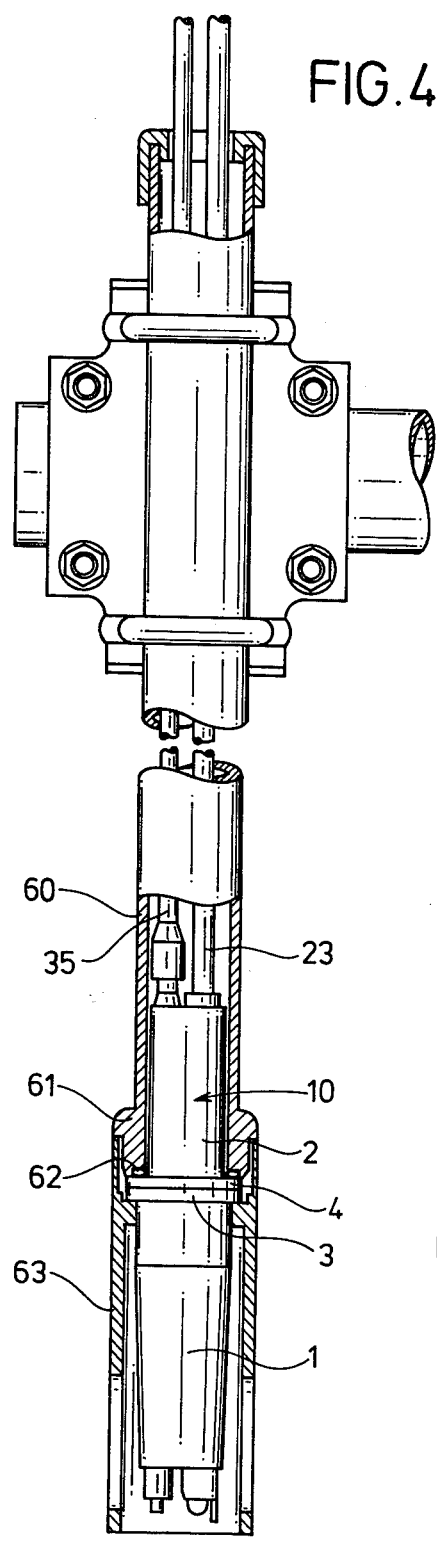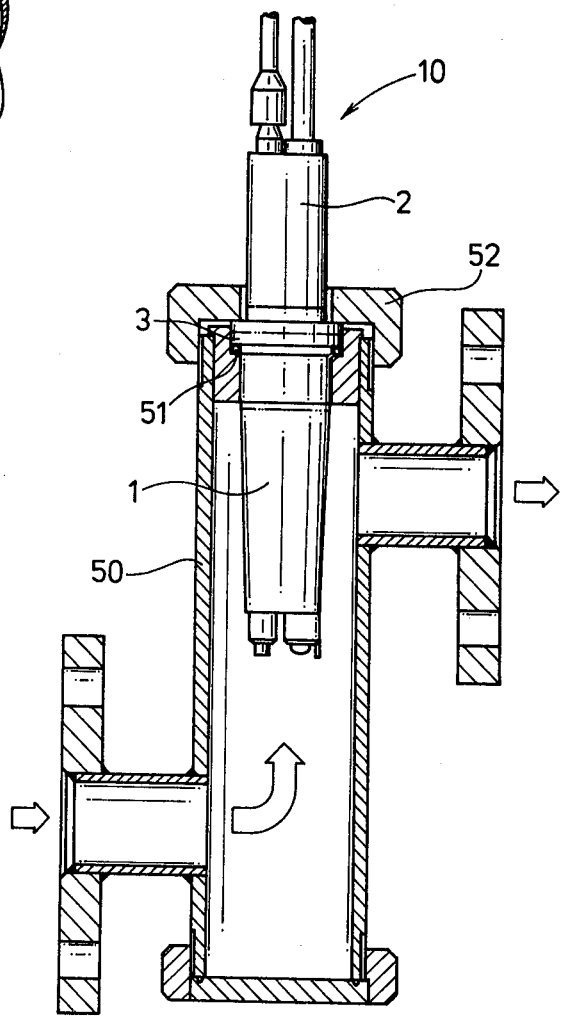

FIG. 9
FIG. 10
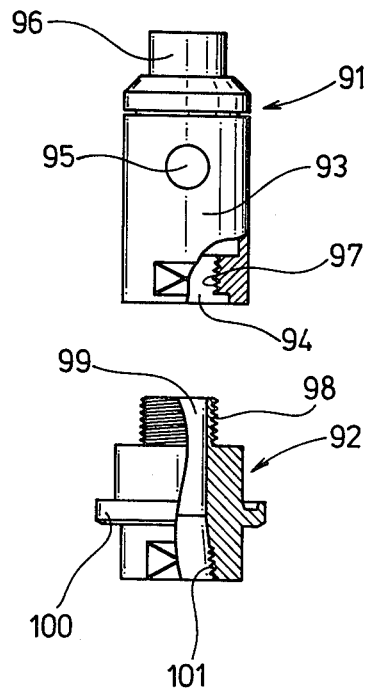
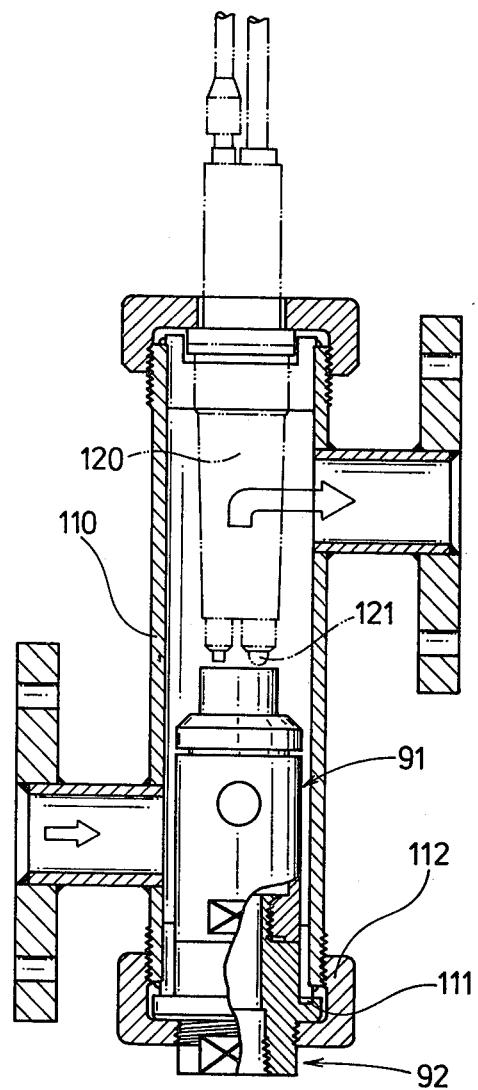

PH SENSOR

BACKGROUND OF THE INVENTION

1. Field of the Invention

This invention relates to a pH sensor for continuously measuring the pH of a test solution, such as in industrial applications.

2. Description of the Prior Art

A wide variety of kinds and types of pH sensors have been used for industrial applications. They are, for example, classified according to the manner in which they are used, such as continuous flow type, immersion type, and submersion type pH sensors. The construction of the sensor is grouped roughly into single purpose and composite types. In addition, pH sensors include liquid junctions either with or without a KCl solution supply.

The various forms of pH sensors are needed to meet different conditions in which the test solutions are available for measurement. Those pH sensors which are best suited for the various test solution conditions are selected for best results. Having pH sensor structures which are different for single or composite pur- poses, however, is disadvantageous in terms of expense of fabrica- tion and expense of maintenance.

The pH sensors usually include electrodes having a detecting end which can be cleaned by a cleaning unit mounted on the pH sensor. The cleaning unit usually comprises a brush positioned immediately below the electrode or sensor unit of the pH sensor. The brush can be rotated by a motor while the brush is being brought into contact with the sensor unit, to scrape deposits off the sensor unit. With such a conventional cleaning unit, the deposits which are scraped off the sensor unit, are then attached to the brush. Disadvantageously, this shortens the service life of the brush. Since the brush is electrically powered for rotation thereof, the seal and power transmission mechanism which are used therein, are complex and hence make such prior cleaning unit expensive.

There are also known various other cleaning units for cleaning pH sensor units or electrodes. They include, for example, ultrasonic cleaners, jet cleaners, and brush cleaners. These cleaning units have their own advantages and disadvantages, and are selectively used to suit the kind of solution which is to be measured. The pH sensors of the continuous flow type, immersion type and submersion type, are equipped with varying cleaning units of their own unique design, and are hence incompatible with each other. Furthermore, cleaning units which operate on different cleaning principles, cannot be used with pH sensors which may however, be used in the same type of use, such as continuous flow, immersion, or submersion.

Accordingly, there exists in the art a deficiency in pH sensors, which needs to be fulfilled.

SUMMARY OF THE INVENTION

This invention aims to overcome the aforementioned and other difficulties, deficiencies and disadvantages of the prior art.

It is a first object of the present invention to provide a pH sensor which can be used in any type of installation, such as continuous flow type, immersion type, or submersion type.

A second object of the invention is to provide a pH sensor assembly with a cleaning unit which is relatively simple in construction, and easy to maintain.

A third object is to provide a pH sensor assembly, including a readily replaceable cleaning unit for use as a continuous flow type, an immersion type, or a submersion type assembly.

The aforementioned first object is achieved by a pH sensor comprising a sleeve assembly having at least first and second spaces, a partition separating the two spaces from each other with a watertight seal, and a barrel including a flange, a reference electrode accommodated in the first space and including a liquid junction, a glass electrode having a sensor unit disposed adjacent to the liquid junction, liquid grounding means mounted adjacent to the liquid junction, and a cable disposed in the second space with a watertight seal, the cable being electrically connected to the reference electrode, the glass electrode and the liquid grounding means and a thermo sensor. With this arrangement, the pH sensor can be used in any of the aforementioned types of installations, and can be inexpensively fabricated and easily maintained.

The aforementioned second object is achieved by a pH sensor combined with a cleaning unit including a runner having a rotatable shaft and a vane unit mounted thereon, and a brush attached to one end of the rotatable shaft. Fluid applied against the vane unit causes rotation of the shaft. The sensor unit is cleaned by the brush when the rotatable shaft is lifted, by force of the fluid applied through the shaft, toward the sensor unit and rotated about its own axis by action of the fluid applied against the vane unit. The shaft has a hole therein through which the fluid flows. The fluid also is used to clean the sensor and the brush. The cleaning unit is simple in construction and can be easily maintained.

The aforementioned third object is achieved by a pH sensor combined with a cleaning unit installed in a working position by an attachment detachably connected to the cleaning unit and can be actuated for cleaning the pH sensor by energy supplied from energy supply means, the cleaning unit being disposed in confronting relation to the sensor unit to be cleaned. The cleaning unit can be replaced with a new unit and can be used in continuous flow type, immersion type or submersion type of pH sensor assembly.

The above and other objects, features and advantages of the present invention will become more apparent from the following description when taken in conjunction with the accompanying drawing wherein preferred embodiments of the present invention are shown by way of illustrative examples.

BRIEF DESCRIPTION OF DRAWINGS

FIGS. 2A and 2B are longitudinal cross sectional views of a pH sensor, having no KCl solution supply, according to another illustrative embodiment, with the two views being taken along orthogonally different planes.

FIG. 3 is a longitudinal cross sectional view of a pH sensor arrangement, of a continuous flow type, utilizing the pH sensor shown in FIGS. 1A through 1C.

FIG. 4 is a longitudinal cross sectional view of a pH sensor arrangement of an immersion type, utilizing the pH sensor shown in FIGS. 1A through 1C.

FIG. 9 is a partly cut away elevational view of a brush cleaning unit for use with the inventive pH sensor.

FIG. 10 is a longitudinal cross sectional view of a cleaning unit assembly wherein the inventive pH sensor of a continuous flow type, is mounted.

DESCRIPTION OF PREFERRED EMBODIMENTS

Figure 1A:
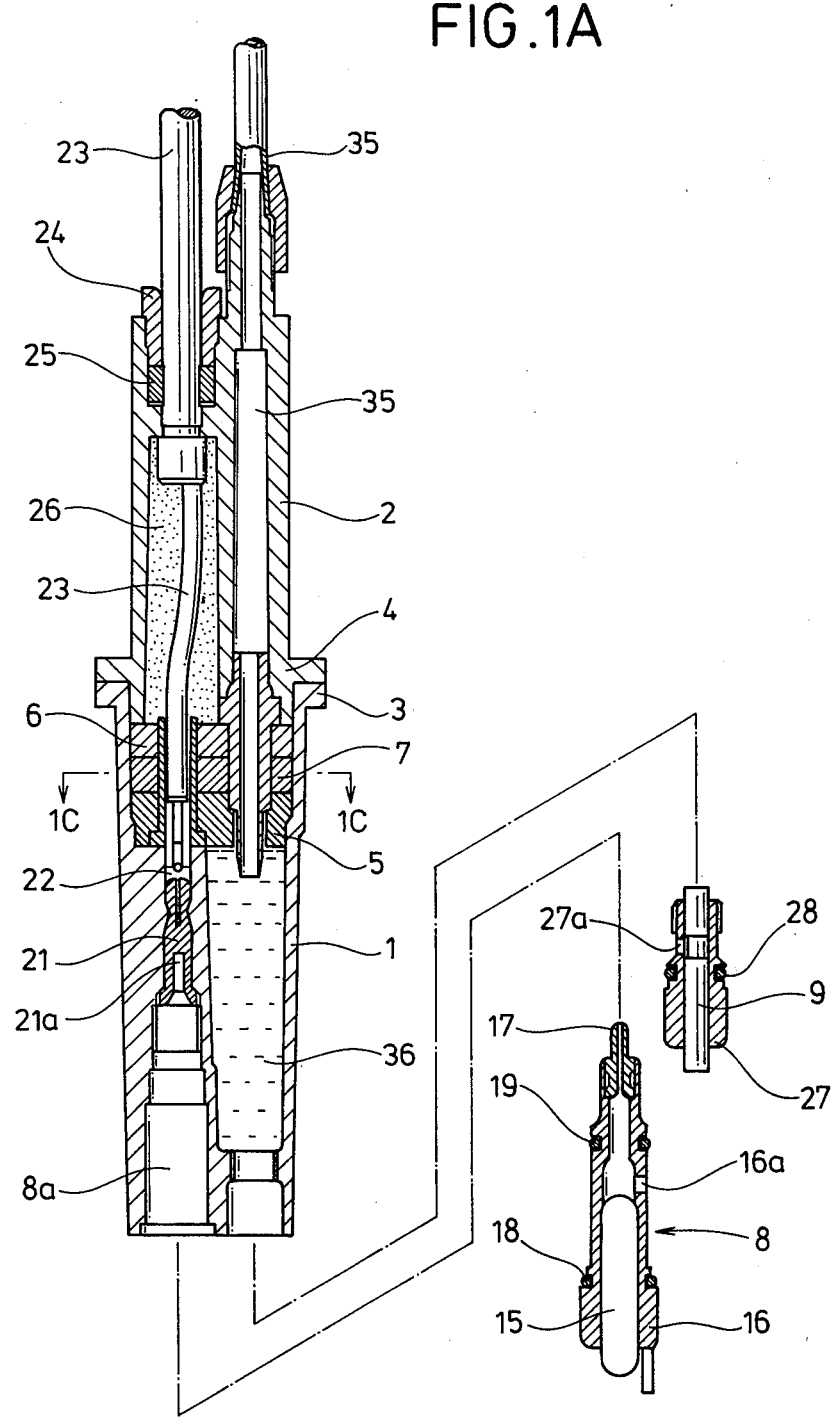
FIG. 1A is a longitudinal cross sectional view of a pH sensor, having a KCl solution supply, according to an illustrative embodiment of the present invention.
Figure 1B:
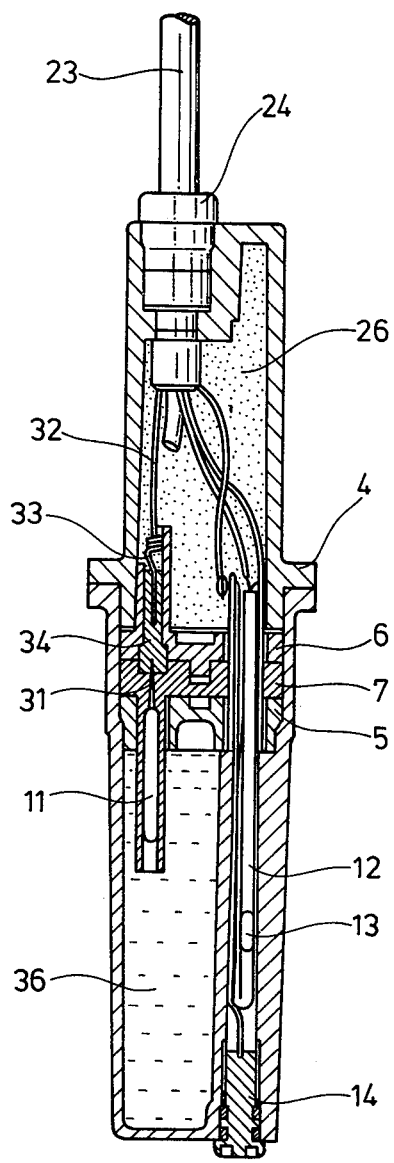
FIG. 1B is a longitudinal cross sectional view of the pH sensor shown in FIG. 1A, with the view being taken along an orthogonally different plane.
Figure 1C:
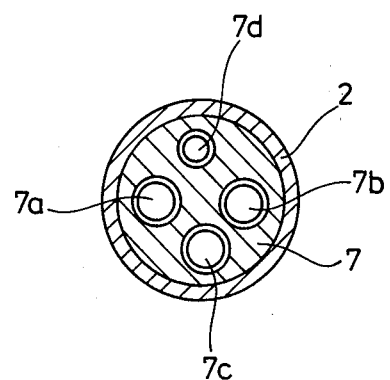
FIG. 1C is a transverse cross sectional view taken along line 1C—1C in FIG. 1A.

Turning to FIGS. 1A through 1C, an illustrative pH sensor includes two sleeves, 1 and 2, made of thermoplastic resin, for example, and having flanges 3 and 4, respectively, which are ultrasonically welded, for example, into a unitary structure. Sleeve 1 contains therein spacers 5 and 6, made, for example, of thermoplastic resin, and a rubber gasket 7 interposed between spacers 5 and 6. Each of spacers 5 and 6 and rubber gasket 7, has a plurality of through holes 7a through 7d (FIG. 1C) through which extend a glass electrode, a KCl solution supply tube, a protective tube and an inner electrode member of a reference electrode, as described hereinbelow in greater detail.

The pH sensor also includes a glass electrode 8 disposed in a cavity 8a defined in sleeve 1, a liquid junction 9 of a reference electrode, an inner electrode 11 (FIG. 1B) of the reference electrode, and a protective tube 12 housing therein temperature sensor 13 and a liquid grounding terminal 14. Glass electrode 8 is composed primarily of a sensing unit 15, a cap 16 accommodating the sensing unit 15 therein, a contact 17 and O-rings 18, 19. Glass electrode 8 is mounted in cavity 8a at a distal end of sleeve 1 and is electrically connected via a conductive rubber body 21 and a contact 22 to a core of a cable 23.

The cores of cable 23 are connected to inner electrode 11 of the reference electrode, temperature sensor 13 and liquid grounding terminal 14. Cable 23 is fixedly mounted on sleeve 2 with a watertight seal provided by a cap 24 made, for example, of thermoplastic resin, a gasket 25, and a filler material 26. Liquid junction 9 of the reference electrode includes a cap 27 and an O-ring 28 and is detachably threaded in sleeve 1. Inner electrode 11 (see FIG. 1B) of the reference electrode has a contact 31 connected through a conductive rubber body 34 to a contact 33 of core 32 of cable 23. The term core (s) used herein refers to, for example, conductive leads, cores, terminals, wires, and the like, which may be covered by non-conductive coverings, which are sometimes termed cables(s). A KCl solution supply tube 35 is mounted in sleeve 2 and serves as a passage for supplying a KCl solution into a KCl solution reservoir 36 defined in sleeve 1.

The cap 24 and spacers 5 and 6 are ultrasonically welded to sleeves 2 and 1, respectively, with no adhesive used. These members, therefore, are not subjected to thermal stresses, which would otherwise be caused by different coefficients of thermal expansion, and hence will be securely retained together against separation. Rubber gasket 7 through which inner electrode 11 of the reference electrode and cable core 23 are interconnected has a Young's modulus E far smaller than that of resin (of sleeves 1,2) so that rubber gasket 7 undergoes a thermal stress (which is proportional to $\alpha \cdot E \cdot T$, wherein $\alpha$ is the coefficient of thermal expansion, E is Young's modulus, and T is temperature difference) sufficiently smaller than that of resin for thereby providing a complete seal.

Inner electrode 11 and core 32 are electrically connected to each other by inserting contact 31 into one end of a conductive rubber body 34 molded intimately onto rubber gasket 7 and inserting contact 33 into the other end of conductive rubber body 34. With conductive rubber body 34 molded on rubber gasket 7, core 32 and the KCl solution reservoir 36 are completely separated from each other with a water tight seal therebetweeen. Contacts 31 and 33 are in the form of a needle which can easily penetrate conductive rubber body 34. Liquid junction 9 is cylindrical in shape and has a reduced diameter portion. A filler material is introduced through an inlet hole 27a in cap 27 around the reduced diameter portion of liquid junction 9. After the filler material has been solidified, it serves as a wedge or retainer to hold liquid junction 9 in place against dislodgement under internal and external pressure acting on the pH sensor.

Sensor unit 15 of glass electrode 8 is secured to cap 16 by a filler material introduced through an inlet hole 16a in cap 16. Sensor unit 15 is electrically connected to cable 23 by inserting contact 17 into a female contact 21a defined in one end of conductive rubber body 21 and inserting a contact 22, connected to the core of cable 23, into the other end of conductive rubber body 21. Since cable 23 and tube 35 are securely attached to the sleeve assembly, the pH sensor can be used as a submersion type pH sensor.

FIGS. 3 and 4 show pH sensor assemblies of the continuous flow type and the immersion type, respectively, incorporating therein the pH sensor shown in FIGS. 1A through 1C.

As shown in FIG. 3, the sensor assembly of a continuous flow type, includes a solution flowing chamber 50 having an O-ring seal 51 through which extends pH sensor 10 into solution flowing chamber 50, pH sensor 10 being attached in position by a cap nut 52. The pH sensor assemby measures the pH of a solution flowing through chamber 50 in the direction of the arrows. With pH sensor 10 mounted in place, sleeve 1 below flange 3 is disposed in the flow of the solution in chamber 50 and sleeve 2 is positioned outside of chamber 50.

In FIG. 4, an immersion sensor assembly comprises a holder pipe 60 having a distal end 61 from which cable 23 and tube 35 are inserted. The pH sensor 10 is mounted on holder pipe 60 by threading a cover 63 onto the distal end 61 of holder pipe 60 with an O-ring 62 serving as a seal between distal end 61 and flange 4 of pH sensor 10. In operation, the immersion sensor assembly is immersed in a process solution up to distal end 61 of holder pipe 60 for measuring the pH of the process solution. With this immersion sensor assembly, cable 23 and tube 35 extend in the axial direction of sleeve 2 within the diameter thereof, so that holder pipe 60 can be of an inside diameter equal to the outside diameter of sleeve 2 throughout its length.

The pH sensor 10 can thus be attached to solution flowing chamber 50 (see FIG. 3) or immersion holder pipe 60 (see FIG. 4) with ease. It can also be used as a submersion type pH sensor. Thus, the pH sensor of the invention finds use in various types of installations.

Figure 2B:
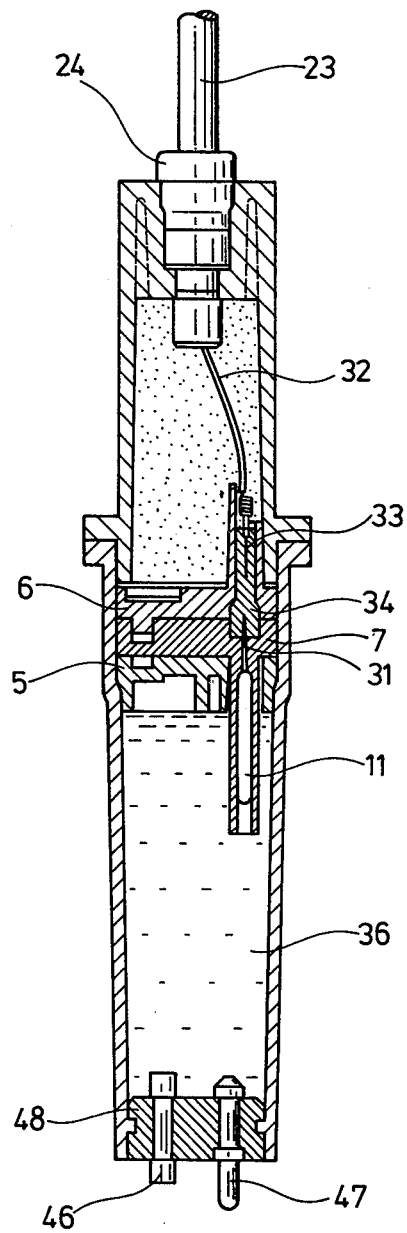
Figure 2C:
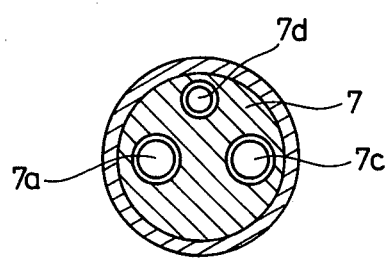
FIG. 2C is a transverse cross sectional view taken along line 2C—2C in FIG. 2A.

FIGS. 2A through 2C illustrate a pH sensor, having no KCl solution supply, according to another illustrative embodiment. Like or corresponding parts in FIGS. 2A through 2C are denoted by like or corresponding reference character in FIGS. 1A through 1C, and will not be described hereat for sake of clarity. These parts operate in the same manner as in FIGS. 1A–1C.

A pH sensor having no KCl solution supply, should preferably be less costly, because it usually is disposed of after use. For this reason, a glass electrode 41 having a sensor unit 44, and a protective tube 45, housing therein a temperature sensor 42 and a liquid grounding terminal 43, are made of glass. Glass electrode 41 and protective tube 45 have distal ends, which together with a liquid junction 46 and pin 47 (see FIG. 2B) are fixed by a gasket 48 to a distal end of sleeve 1.

The pH sensor, having no KCl solution supply, as described also has flanges on its barrel (i.e., side walls of sleeves 1,2) and a cable fixedly secured to the sleeve, so that the pH sensor can be readily used in any type of installation, such as those having a solution flowing chamber, an immersion holder pipe, etc.

Figure 5A:
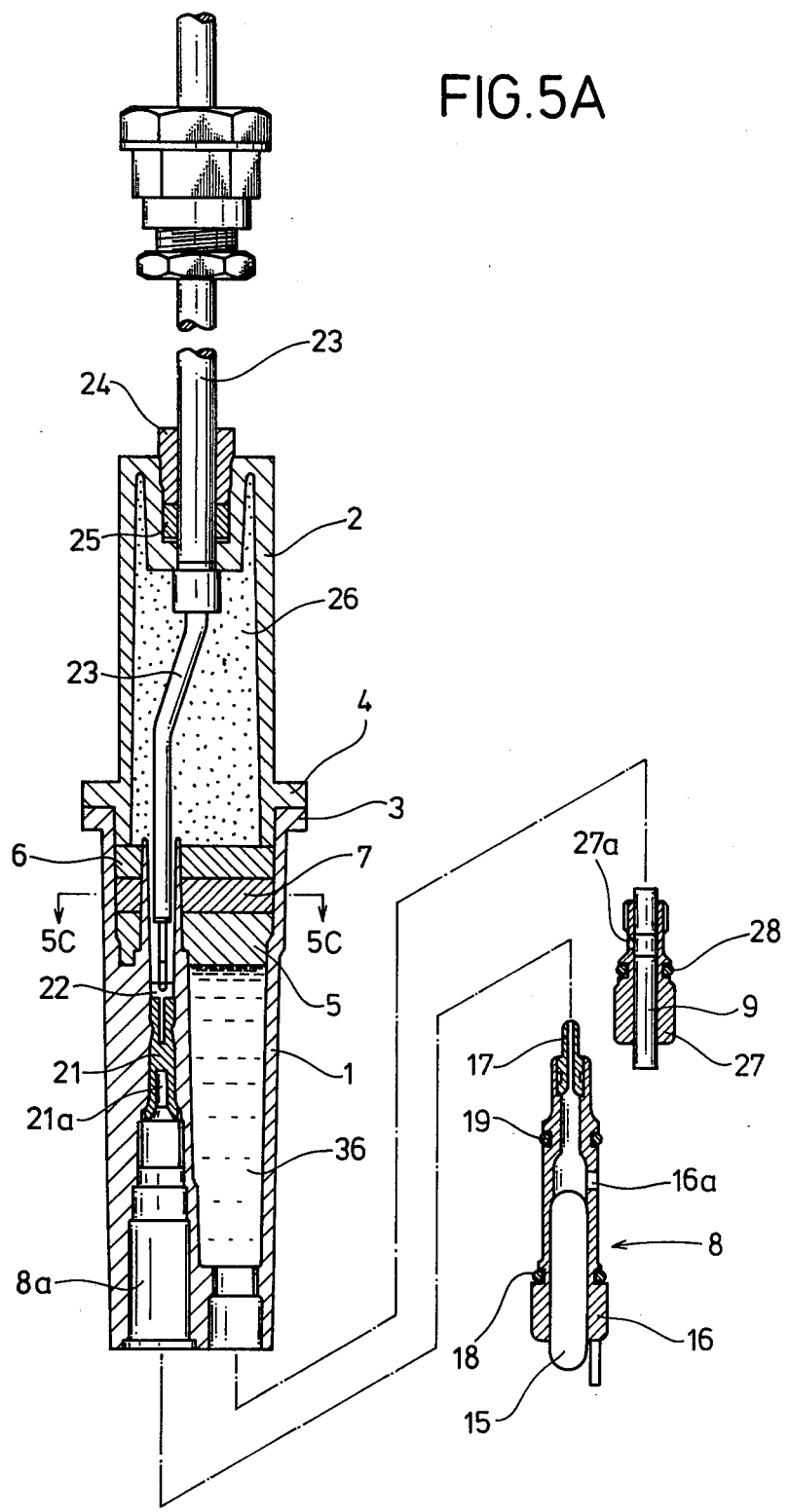
FIGS. 5A and 5B are longitudinal cross sectional views of a pH sensor, having no KCl solution supply, according to still another illustrative embodiment, with the two views being taken along mutually perpendicular planes.
Figure 5B:
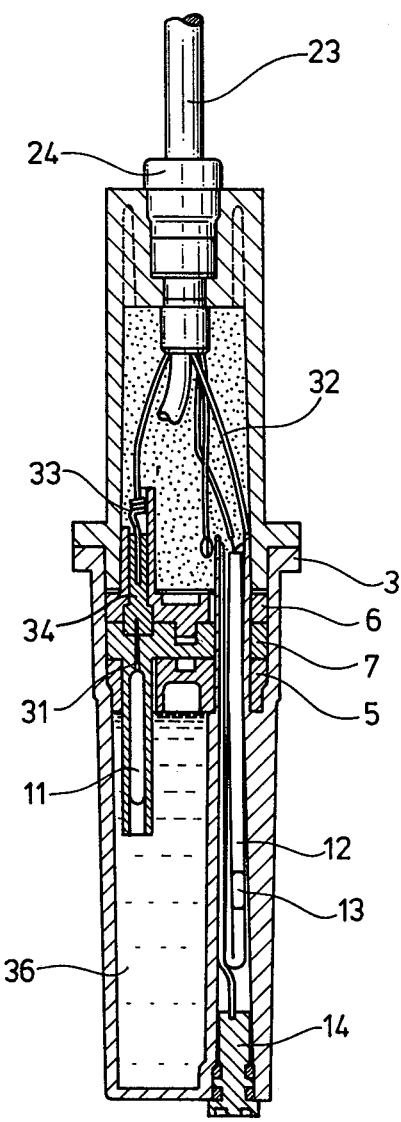
Figure 5C:
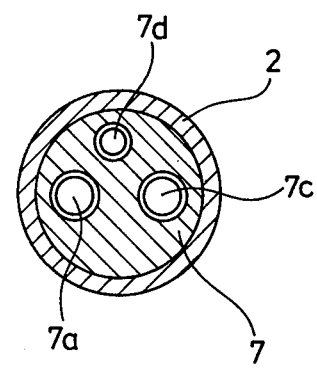
FIG. 5C is a transverse cross sectional view taken along line 5C—5C in FIG. 5A.

FIGS. 5A through 5C show a pH sensor having no KCl solution supply, according to still another illustrative embodiment. Like or corresponding parts in FIGS. 5A–5C are denoted by like or corresponding reference characters in FIGS. 1A–1C, and will not be described hereat for sake of clarity. These parts operate in the same manner as in FIGS. 1A–1C.

The pH sensor, having no KCl solution supply, shown in FIGS. 5A–5C (hereinafter sometimes referred to as "III-type sensor") has a combination of sleeve 1 of the pH sensor having a KCl solution supply (hereinafter sometimes referred to as "I-type sensor") as shown in FIGS. 1A through 1C, and sleeve 2 of the pH sensor having no KCl solution supply (hereinafter referred to as sometimes as "I-type sensor") as shown in FIGS. 2A–2C. Thus, the III-type sensor enjoys the combined advantages of the I-type sensor and the II-type sensor.

More specifically, the I-type sensor can supply a KCl solution and has liquid junction and electrodes, which are replaceable, so that the pH sensor is suitable for use under rough conditions which accelerate wear on the replaceable sensor parts. The II-type sensor, on the other hand, is suited for use under normal conditions, and there is no need to replenish a supply of KCl solution. Thus, the III-type sensor is essentially designed for normal use with no additional supply of KCl solution being needed. Since the liquid junction, the electrodes and internal solution are replaceable, the III-type sensor can be put to use in applications in which the endurance of the sensor can hardly be predicted. Another advantage of the III-type sensor is that it can be constructed of the same chamber and holder pipe as those of the I-type and II-type sensors because the latter sensors have substantially the same sleeves, flanges, cable installations, etc that serve to attach the chamber and holder pipe.

Any one or more of the pH sensors of the present invention, as described above, have a sleeve assembly with a flange on its barrel, a structure which allows the pH sensor to be used in any type of installation, such as the priorly discussed immersion type, continuous type and submersion type. Thus, kinds of pH sensors required can be reduced, and such pH sensors can be more inexpensively manufactured and more readily and easily maintained. In FIGS. 1A–1C, the rubber gasket with conductive rubber body 34, is employed to provide an inside seal which is not subjected to corrosion that would otherwise be the case with a metal gasket. Moreover, the rubber gasket requires no additional seal such as an O-ring. Since sleeves 1 and 2 are ultrasonically welded together the sleeve assembly can be fabricated with ease and is of a rugged construction.

Figure 6:
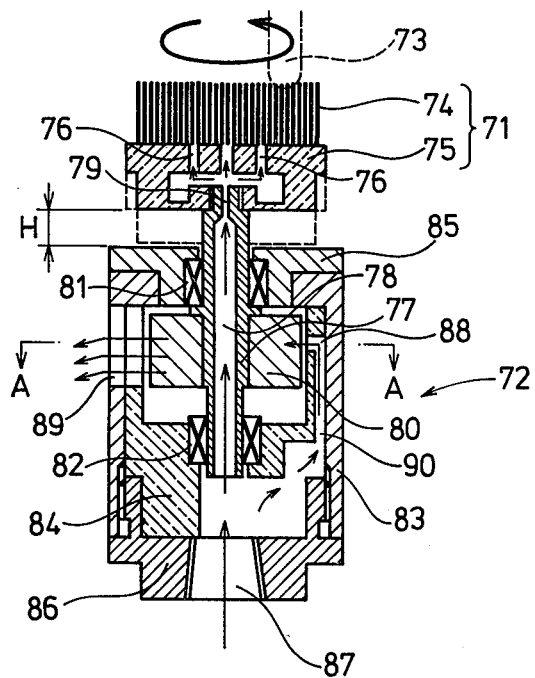
FIG. 6 is a longitudinal cross sectional view of a cleaning unit for use with the inventive pH sensor.

FIG. 6 shows a cleaning unit, which may be mounted on the pH sensor of the present invention. The cleaning unit comprises a brush 71 and a body 72 supporting brush 71, for rotating and vertically displacing the brush 71. Body 72 has a casing 83 supported by a holder (not shown) with brush 71 disposed upwardly below an electrode 73 of the pH sensor unit to be cleaned. Brush 71 is composed of bristles 74 and a base 75 on which bristles 74 are mounted. Base 75 is attached to an upper end of a rotational shaft 77 journalled in a pair of sliding bearings 81,82 mounted in casing 83. Base 75 has spouts 76 communicating with a longitudinal passageway 78 defined through rotational shaft 77 and having a restricted portion 79. Rotational shaft 77 includes a vane unit 80 and is rotatably supported on an upper fastener 85 by sliding bearing 81 and on a lower support or chamber 84 by sliding bearing 82. The vane may be integral with or be attached to the shaft, so that rotation of the vane will rotate the shaft. Rotational shaft 77 serves as a runner rotatable by jet streams (such as of fluid) which are ejected from nozzles 88,88' (see FIG. 8) onto the vane unit 80.

Figures 7, 8:
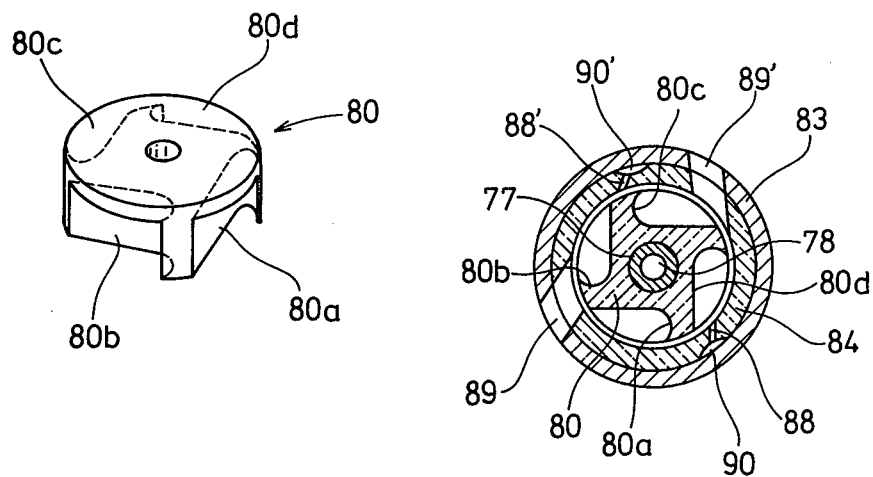
FIG. 7 is a perspective view of a vane unit used in the cleaning unit shown in FIG. 6.
FIG. 8 is a transverse cross sectional view taken along line A—A in FIG. 6.

As shown in FIG. 7, vane unit 80 includes 4 angularly equally spaced vanes 80a, 80b, 80c, and 80d formed by cutting off sidewall portions of a cylindrical vane unit body, for example. Vanes 80a–80d are positioned to receive the jet stream ejected from nozzle 88, 88'. The runner (which comprises rotating shaft 77, brush 71 and vane unit 80) is upwardly displaced under an upward fluid pressure concurrently with the rotation thereof. The upward movement is caused by the fluid being supplied through the restricted portion 79, and moves the brush upward distance "H" to come into contact with the sensor unit to be cleaned. Concurrently, fluid ejected against vanes 80a–80d, causes rotation of the vane unit 80, and hence the rotation of the rotation shaft 77, and further the rotation of the brush 71. When upward fluid pressure is removed, runner 77 is downwardly displaced by force of gravity, by a distance "H", as shown in FIG. 6. Support 84 serves as a base on which sliding bearing 82 is mounted. Support 84 and casing 83 jointly define passageways 90,90′, communicating with nozzles 88,88′, respectively.

To assemble the unit, support 84 is inserted into casing 83 from below, and securely mounted into position therein by a lower fastener 86. Nozzle 88 is supplied with a liquid or gas (hereinafter and before referred sometimes as "fluid") which is introduced through a hole 87 defined through lower fastener 86. After the jet stream of such a fluid from nozzle 88 has impinged on vane unit 80 of runner 77, to cause rotation of the latter, the fluid loses its dynamic energy and is discharged out of casing 83 through discharge ports 89,89′ which extend through casing 83 and support 84, as better shown in FIG. 8. More specifically, the stream of fluid ejected out of nozzle 88 impinges on vanes 80a–80d successively and is then discharged out of discharge port 89′. The stream of fluid coming through passageway 90′ and ejected out of nozzle 88′ impinges on vanes 80a–80d succesively, and is then discharged out of discharge port 89.

In operation, the fluid introduced through a pipe (not shown) coupled with hole 87 into casing 83 is divided into two streams. One stream is directed through passageway 78 to spouts 76. The other stream is ejected as a jet out of nozzle 88 against vane unit 80, as discussed. The fluid flow from nozzle 88 impinges on vanes 80a–80d, to cause rotation of vane 80, and thereby rotates runner 77, and then flows out of the discharge ports 89,89′, as discussed. The fluid flowing through passageway 78 acts on restricted portion 79 to vertically raise runner 77 and is then discharged as jets out of spouts 76. Runner 77 is lifted or upwardly displaced by distance "H" which is limited by upper fastener 85 serving as a stop for runner 77. Distance "H" is selected to be large enough to enable bristles 74 of brush 71 to contact electrode 73.

The fluid streams coming out of spouts 76 perform two functions, first to remove deposits from the bristles 74, and second to remove dirt, or other undesired impurities which may have accumulated on the electrode 73.

Thus, as can be readily appreciated, the fluid as employed in the inventive cleaning unit, functions to vertically lift the brush unit to come into contact with the sensor unit parts to be cleaned, and then causes rotation of the brush unit to clean the parts, and furthermore acts to clean off from the brush, deposits which may have accumulated thereon as a result of cleaning the sensor part. The structure of the cleaning unit of the invention enables the foregoing functions to be performed by the fluid, with ease and reliability. Moreover, advantageously, the structure of the invention is inexpensively fabricated.

After cleaning operation, the fluid is no longer supplied and the shaft 77 falls by gravity action and the brush 71 is removed from contact with the sensor part being cleaned.

Although in the embodiment just described, a restricted portion 79 is used in shaft 77 to provide a mechanism for lifting the shaft to enable the brush to contact the part being cleaned, the spouts themselve are sufficient to enable the fluid to lift the shaft 77. Thus, the lifting mechanism may be either the spouts 76 alone, or in combination with the restricted portion 79. Moreover, passageways 90,90′ which communicate respectively with nozzles 88,88′, may be defined in the side walls of casing 83, or may comprise tubes attached on the exterior of casing 83.

Advantageously, it has been found that the cleaning unit just described, has increased life because the bristles of brush 71, are continuously cleaned of dirt or other deposits. Since runner 77 is powered by pressure of fluids, such as liquid or gas, the cleaning unit, advantageously, is relatively simple in construction, inexpensively made, and is easily maintained.

FIG. 9 is illustrative of a brush cleaning unit which may be used with the pH sensor of the invention. The brush cleaning unit includes a cleaning unit 91 and an attachment 92. Cleaning unit 91 is constructed as shown in FIG. 6 and has a brush 96 which is rotatable and vertically movable under pressure of a fluid which flows through a casing 93 from a hole 94 located at the bottom and toward a discharge port 95, so that brush 96 can clean a sensor unit of a pH sensor (not shown) in contact therewith. Attachment 92 has a screw portion 98, which may be threaded into an internally threaded portion 97 in hole 94 in cleaning unit 91, a through hole 99 held in fluid communication with hole 94,and a flange 100. Through hole 99 has an internally threaded portion 101. Cleaning unit 91 and attachment 92 are assembled together by threaded inter-engagement. The brush cleaning unit, thus assembled, is positioned in close proximity with the sensor unit of the pH sensor to be cleaned with a fluid pipe (not shown), such as for supplying industrial water, being held in threaded engagement with internally threaded portion 101 of attachment 92.

FIG. 10 shows a brush cleaning unit, such as shown in FIG. 9, installed in a pH sensor assembly of the continuous flow type. Cleaning unit 91, with attachment 92 mounted thereon, is placed in a solution flowing chamber 110, and retained therein by an O-ring 111 and a cap nut 112, in confronting relation with a pH sensor 120 fixedly mounted in chamber 110. The brush cleaning unit, as thus disposed in position, has its brush bristles held in contact with sensor unit 121 of a glass electrode in pH sensor 120. During operation of the pH sensor 120, a solution to be measured, flows through chamber 110 in the direction of the arrows.

Figure 11:
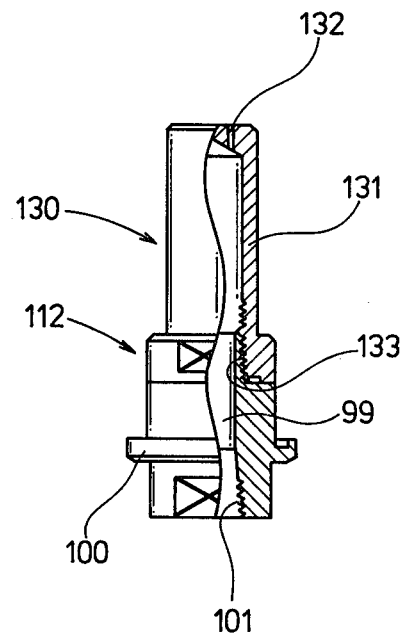
FIG. 11 is a partly cut away elevational view of a jet cleaning unit for used with the inventive pH sensor of a continuous flow type.

FIG. 11 shows a jet cleaning unit, which may be used with a pH sensor, such as disclosed herein. The jet cleaning unit comprises a cleaning unit 130, in the form of a hollow cylinder 131 having in its distal end, a plurality of minute holes 132 and an internally threaded portion 133 in cylinder 131. Cleaning unit 130 is assembled with an attachment 112 having a through hole 99 and including an internally threaded portion 101. A fluid supply pipe (not shown) is connected to internally threaded portion 101 to supply a cleaning fluid into cleaning unit 130, from which cleaning fluid is ejected through holes 132 against a sensor unit part to be cleaned. The jet cleaning unit can be readily installed in the chamber of a pH sensor assembly, for example, of a continuously flowing type.

Figure 12:
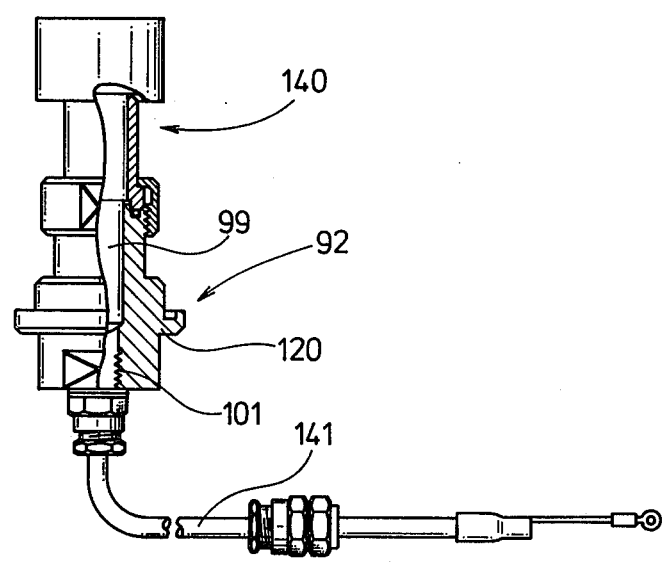
FIG. 12 is a partly cut away elevational view of an ultrasonic cleaning unit for use with the inventive pH sensor of a continuous flow type.

FIG. 12 illustrates an ultrasonic cleaning unit which may be used with the inventive pH sensor. The ultrasonic cleaning unit includes an ultrasonic cleaning unit 140, an attachment 92, and a cable 141. Ultrasonic cleaning unit 140 is electrically connected to the cores of cable 141 which extend through a through hole 99 in attachment 92. Thus, ultrasonic cleaning unit 140 can be energized by an electric current supplied by cable 141. The ultrasonic cleaning unit can also be installed readily in the chamber of a pH sensor assembly, such as used for continuous flow of test solutions.

Figure 14:
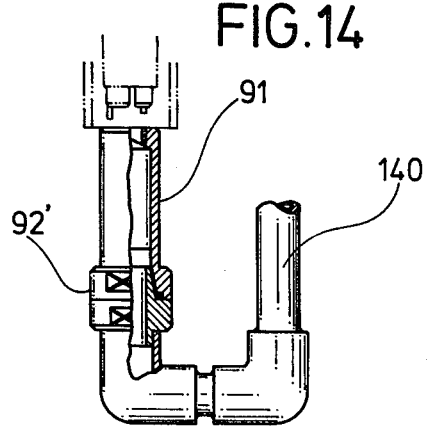
FIG. 14 is an elevational view of a jet cleaning unit assembly wherein is mounted the inventive pH sensor of an immersion type.
Figure 15:
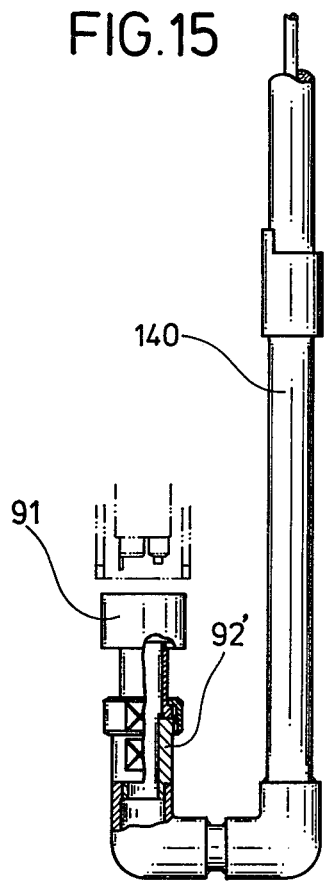
FIG. 15 is an elevational view of an ultrasonic cleaning unit assembly, wherein is disposed the inventive pH sensor of an immersion type.
Figure 13:
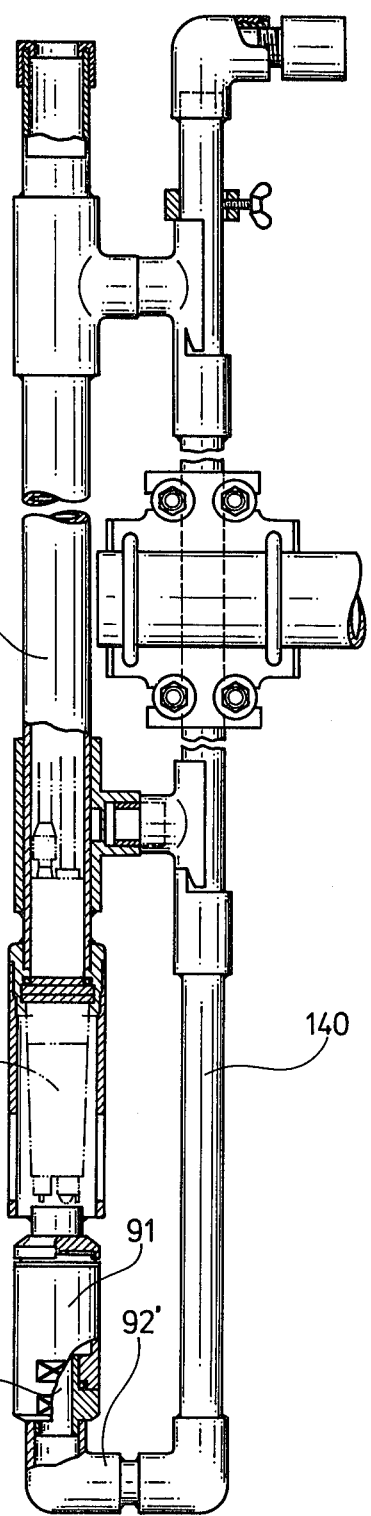
FIG. 13 is an elevational view of a brush cleaning unit assembly, wherein is installed the inventive pH sensor of an immersion type.

FIG. 13 shows a brush cleaning unit, such as shown in FIG. 9, as mounted in an immersion type pH sensor assembly. FIG. 14 illustrates a jet cleaning unit, such as shown in FIG. 11, as installed in an immersion type pH sensor assembly. FIG. 15 illustrates an ultrasonic cleaning unit, such as shown in FIG. 12, as combined with an immersion type pH sensor assembly.

The respective cleaning units, as mounted in an immersion type pH sensor assembly, include a cleaning unit 91 attached to a holder 140 by an L-shaped attachment 92' (see FIGS. 14 and 15). The cleaning unit holder 140 provides a fluid flow passage or houses an electrical cable therein. (see FIG. 13).

The brush cleaning unit, jet cleaning unit, and ultrasonic cleaning unit, can be easily installed and replaced, and furthermore can be used in different types of installations, such as immersion, continuous flow, or submersion. With the arrangement of the cleaning unit for use with the pH sensors of the invention, advantageously, the cleaning unit can be detached readily and readily replaced with another cleaning unit, or parts thereof. The detachable attachment on such cleaning units, facilitates such ready replacment.

Furthermore in reference to the pH sensors of the invention, in some embodiments there is used a KCl solution supply, and in some other embodiments there is not used any KCl solution supply. What is meant by that description is that in each embodiment there is a KCl solution reservoir 36, but that in some embodiments there is a supply tube 35 which supplies the KCl solution to the reservoir, whereas in other embodiments no supply tube is used. Thus, in the first embodiments, the solution may flow in and out of the reservoir, whereas in the latter embodiments, the solution does not flow out of the reservoir.

The foregoing description is illustrative of the principles of the invention. Numerous other modifications and extensions thereof would be apparent to the worker skilled in the art. All such modifications and extensions are to be considered to be within the spirit and scope of the invention.

What is claimed is:

1. A pH sensor comprising
a sleeve assembly having a side wall and defining at least first and second spaces, a partition providing water tight separation between said first and second spaces, and a flange projecting outwardly from said side wall;
a reference electrode comprising an electrolytic solution accommodated in said first space, an inner electrode, and a liquid junction positioned at one end of said sleeve assembly;
a glass electrode comprising a sensor unit, disposed adjacent to said liquid junction;
liquid grounding means disposed adjacent to said liquid junction;
cable means inserted through an opening formed at the other end of said sleeve assembly and electrically connected to said reference electrode, said glass electrode, and said liquid grounding means; and
means for holding said cable means with a water tight seal within said second space; wherein
said sleeve assembly further defines a first cavity and a second cavity; annd wherein said glass electrode is replaceably disposed within said first cavity, and said liquid junction is replaceably disposed within said second cavity.

2. The sensor of claim 1, said partition comprises a rubber gasket and a conductive rubber body molded intimately thereon.

3. The sensor of claim 1 or claim 2, wherein said flange includes flange members ultrasonically welded together.

4. The sensor of claim 1, wherein said electrolytic solution of said reference electrode is nonflowable out of said first space.

5. The sensor of claim 1, wherein electrolytic solution of said reference electrode is flowable out of said first space.

6. The sensor of claim 5, wherein said sleeve has an opening in said other end thereof and a passageway communicating with said opening for supplying an electrolytic solution for said reference electrode.

7. The sensor according to claim 1, further including a cleaning unit means comprising an assembly including a rotatable shaft having a longitudinal passageway therethrough with means for restricting flow of fluid therethrough, sliding bearings by which said shaft is rotatably journalled, and a vane unit connected to said rotatable shaft, a nozzle for ejecting a stream of fluid against said vane unit to rotate said rotatable shaft, and a brush mounted on said rotatable shaft and having spouts communicating with said passageway in said rotatable shaft, said brush being disposed substantially below said sensor with said rotatable shaft substantially aligned therewith vertically, said rotatable shaft being rotatable and axially movable toward said sensor unit under presure of said fluid flowing out of said nozzle and through said passageway and through said means for restricting flow of said fluid, whereby said sensor unit is cleaned by fluid jetting from said spouts and by rotation of said brush, and said brush is concurrently cleaned by said fluid.

8. The sensor according to claim 1, including a cleaning unit means comprising a cleaning unit having a cleaning member on its distal end, an attachment having a through passageway therein and detachably connected to said cleaning unit, and means for supplying power for driving said cleaning member through said through passageway in said attachment, said cleaning unit being positioned in confronting relation to said sensor unit, whereby said sensor unit is cleanable by said cleaning unit.

9. The sensor of claim 8, wherein said cleaning unit comprises a brush cleaning unit.

10. The sensor of claim 8, wherein said cleaning unit comprises a jet cleaning unit.

11. The sensor of claim 8, wherein said cleaning unit comprises an ultrasonic cleaning unit.

* * * * *